United States Patent [19]

Bähnisch

[11] 4,326,041

[45] Apr. 20, 1982

[54] PROCESS FOR THE CATALYTIC SYNTHESIS OF METHANOL

[75] Inventor: Hans-Joachim Bähnisch, Dortmund, Fed. Rep. of Germany

[73] Assignee: UHDE GmbH, Dortmund, Fed. Rep. of Germany

[21] Appl. No.: 177,093

[22] Filed: Aug. 11, 1980

[30] Foreign Application Priority Data

Aug. 24, 1979 [DE] Fed. Rep. of Germany ....... 2934332

[51] Int. Cl.$^3$ ...................... C07C 27/06; C07C 31/04
[52] U.S. Cl. .................................. 518/702; 518/703; 518/704; 518/712; 165/1
[58] Field of Search ............... 518/712, 703, 704, 702; 165/1

[56] References Cited

U.S. PATENT DOCUMENTS 3,531,266 9/1970 Chernoff ............................ 518/704
4,065,483 12/1977 Pinto .................................. 518/704

FOREIGN PATENT DOCUMENTS 1316705 5/1973 United Kingdom ................ 518/704

OTHER PUBLICATIONS

Pinto et al., Ampo 78, ICI Symposium on $NH_3$ & Methanol, Jun. 7-9, 1978, paper 2.
Petroleum Refiner, vol. 34, No. 12, pp. 165-167, 1955.

*Primary Examiner*—Howard T. Mars
*Attorney, Agent, or Firm*—Wilson, Fraser, Barker & Clemens

[57] ABSTRACT

The invention relates to a process for the catalytic synthesis of methanol from a raw gas which mainly contains CO, $CO_2$ and $H_2$ and is obtained in a catalytic natural-gas cracking plant, the raw gas being compressed in several stages to the synthesis pressure of 50-150 bar and gas being purged from the synthesis loop in order to maintain a given inert gas level.

2 Claims, 1 Drawing Figure

PROCESS FOR THE CATALYTIC SYNTHESIS OF METHANOL

BACKGROUND OF THE INVENTION

The process for the catalytic synthesis of methanol from a raw gas which mainly contains CO, $CO_2$ and $H_2$ usually comprises three sections, namely the cracking of natural gas to raw gas, compression of the raw gas to the required synthesis pressure and the catalytic synthesis itself. Intense heat (e.g. 700°–1200° C.) is required for cracking the natural gas. Then the raw gas must be cooled to ambient temperature (20°–40° C.) in order to be compressed from approx. 10–30 bar to approx. 50–150 bar, the compression equipment requiring a large amount of energy. The subsequent catalytic synthesis of methanol proceeds at medium temperatures (200°–300° C.) and yields cooled gas and condensed methanol. In order to maintain a permissible inert gas level in the synthesis loop, a certain amount of loop gas is continuously purged from the loop. This gas, known as purge gas, contains a considerable amount of combustible energy carriers such as CO and $H_2$ and is purged from the loop via a relief valve and incinerated at a low pressure in the cracking furnace. Although, with the methanol process described above, the energetical relations between the cracking, compression and synthesis processes are balanced, energy management in, and the reliability of, the compression section have so far been neglected. The heat of compression was thus completely dissipated to the cooling water and stand-by cooling water pumps had to be provided to ensure effective inter-stage and final cooling of the synthesis gas.

SUMMARY OF THE INVENTION

The aim of the invention is to link the three sections, namely the gas cracking, compression and methanol synthesis sections in a suitable way to eliminate the disadvantages described above.

This aim is achieved by this invention in that the natural gas to be converted and the pressurized purge gas are passed through a section of the inter-stage cooler and of the aftercooler of the synthesis compressor in order to absorb heat.

In order to further promote the recovery of energy, the purge gas, which is heated to a temperature of above 150° C. is fed to an expansion turbine before being used at a low pressure as fuel in the cracking furnace.

The advantages achieved by the invention are mainly that a coolant always flows through the inter-stage cooler and the aftercooler of the synthesis gas compressor and the heat of compression is recovered at a high temperature level. The coolant for the inter-stage cooler is natural gas and purge gas, which is available at a pressure of approx. 30–40 bar and 50–100 bar, respectively. Purge gas also flows through the aftercooler. Even in the event of failure of the cooling water, both gases always flow through the inter-stage cooler, which means that no overheating can occur due to lack of cooling in the subsequent synthesis gas compression steps. The bearings and shafts of the synthesis gas compressor always remain in the operating temperature range. The natural gas preheater acting as the inter-stage cooler or aftercooler of the compressor exhibits roughly the same operating pressures on the gas and shell sides, i.e. medium pressure of approx. 10–30 bar and high pressure of 50–100 bar, as the case may be. The heat exchanger tubes are thus subjected to almost no pressure difference during operation. Preheating the natural gas for heating purposes and generation of product gas permits a considerable reduction of the heat exchange surface of the air preheater in the flue gas duct of the cracking furnace owing to more favourable flue gas temperatures.

It is not necessary to use materials of any particular alloys because no condensate is formed as a result of the temperature dropping below the dew point in the inter-stage cooler and the aftercooler for synthesis gas.

BRIEF DESCRIPTION OF THE DRAWINGS

The process is described below and is illustrated in the flow diagram of FIG. 1 which represents a preferred configuration.

DESCRIPTION OF PREFERRED EMBODIMENT

Figure 1:
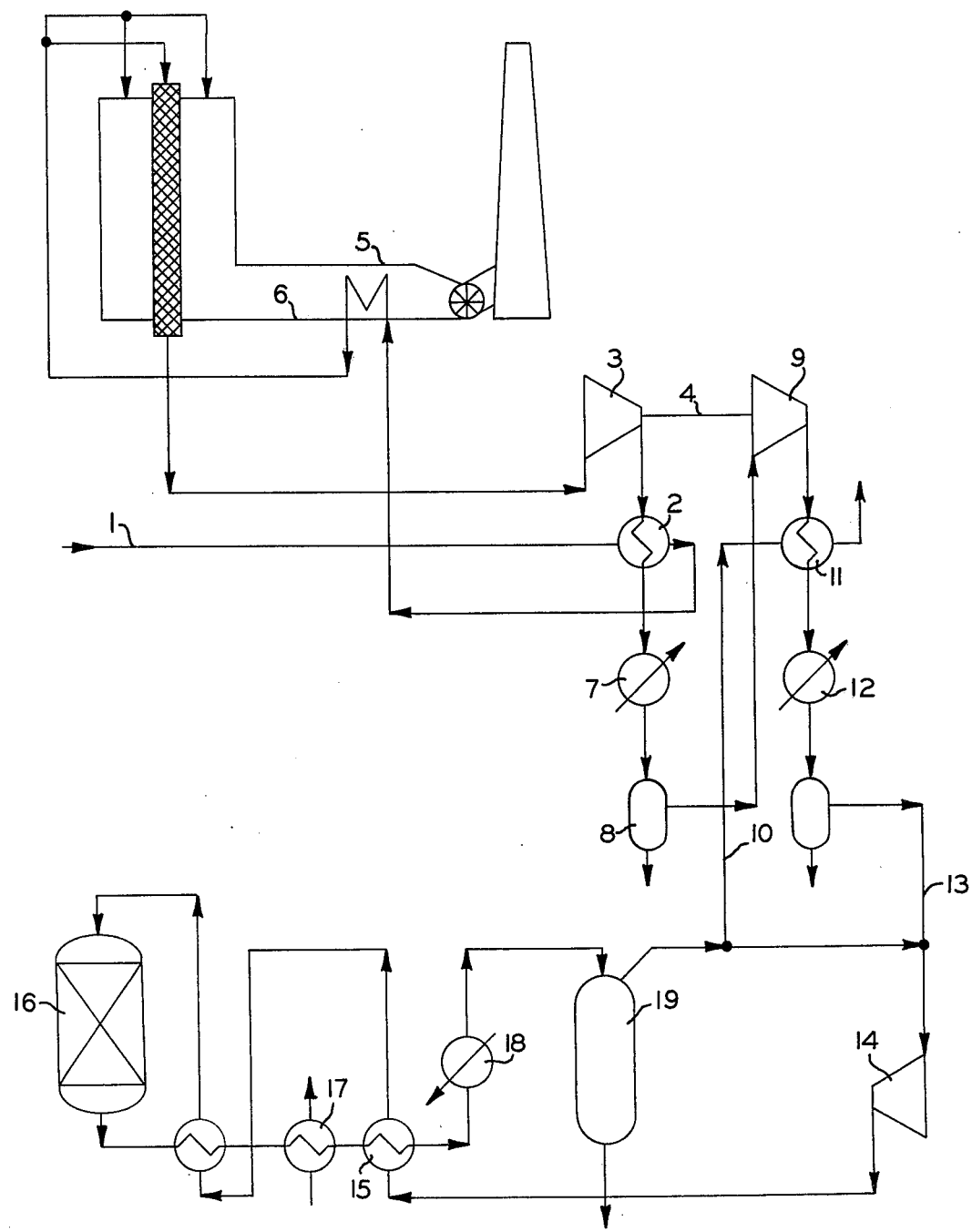

The flow diagram of FIG. 1 illustrates the flue gas duct of the cracking furnace, the synthesis gas compressor and the methanol synthesis unit. The natural gas, which is fed to the plant via line 1 is heated in the inter-stage cooler 2 of the first stage 3 of the synthesis gas compressor 4 from approx. 40° C. to approx. 140° C., next flows to the natural gas heater 5 in the flue gas duct 6, and is then split into the fuel gas and the product gas part-stream for the cracking furnace.

As a result of heating the natural gas, the synthesis gas from the first stage is cooled to approx. 125° C. It is further cooled to approx. 40° C. in the water cooler 7. After the condensate is separated in the separator 8, the synthesis gas, which is compressed to approx. 41 bar, enters the last stage 9 of the synthesis gas compressor, where it is compressed to approx. 100 bar. It leaves the compressor at a temperature of approx. 173° C. The ethalpy of the synthesis gas is high enough to heat the purge gas in line 10 from the methanol synthesis section in the aftercooler 11 from approx. 40° C. to approx. 165° C. The heated purge gas can either be fired directly or, if the quantity is sufficient, passed through an expansion turbine, where its pressure is reduced to pe=approx. 2–5 bar, in order to recover driving energy. After being compressed to approx. 100 bar, the synthesis gas enters the water cooler 12 at a temperature of approx. 136° C. and is cooled to approx. 40° C. Then it is fed via line 13 to the methanol synthesis loop, which comprises the recycle compressor 14, heater 15, synthesis reactor 16, waste heat boiler 17, final cooler 18 and separator 19. The liquid product, i.e. methanol is removed from the bottom of the separator 19 and any unreacted, unconverted loop gas is removed from the top and fed to the recycle compressor. In order to maintain an optimum inert gas level in the loop, a certain amount of gas is purged from the loop. Synthesis gas is added to the remaining quantity of loop gas as described above.

I claim:

1. In a process wherein natural gas feed is cracked in a natural gas cracking plant to produce a raw gas which contains CO, $CO_2$ and $H_2$, the raw gas is compressed in several stages to a synthesis pressure of 50–150 bar, cooled and converted to methanol in a catalytic synthesis loop while gas is purged from the synthesis loop to maintain the inert gas level therein below a given limit, the improvement comprising exchanging heat to natural gas feed for the natural gas cracking plant from compressed raw gas at an intermediate stage of compression and exchanging heat to the purged gas from the finally-compressed raw gas.

2. The improvement according to claim 1, wherein the heat transferred to the gas purged from the synthesis loop is effective to heat the purged gas to a temperature of above 150° C., the heated purge gas is expanded, and the expanded purge gas is fed to the natural gas cracking plant as fuel.

* * * * *